(12) United States Patent
Zhang et al.

(10) Patent No.: US 11,795,254 B1
(45) Date of Patent: *Oct. 24, 2023

(54) PERFLUORO COPOLYMERS

(71) Applicant: Sparkling Tycoon Limited, Mahe (SC)

(72) Inventors: Hao Zhang, Los Gatos, CA (US); Yuanxi Liao, Pittsburgh, PA (US)

(73) Assignee: Sparkling Tycoon Limited, Mahe (SC)

( * ) Notice: Subject to any disclaimer, the term of this patent is extended or adjusted under 35 U.S.C. 154(b) by 0 days.

This patent is subject to a terminal disclaimer.

(21) Appl. No.: 17/891,018

(22) Filed: Aug. 18, 2022

Related U.S. Application Data

(63) Continuation of application No. 17/741,391, filed on May 10, 2022, now Pat. No. 11,485,814.

(51) Int. Cl.
  *C08F 224/00* (2006.01)
  *C07D 317/42* (2006.01)
  *C07D 317/00* (2006.01)
  *C07D 319/06* (2006.01)
  *C08F 34/02* (2006.01)

(52) U.S. Cl.
  CPC .......... *C08F 224/00* (2013.01); *C07D 317/00* (2013.01); *C07D 317/42* (2013.01); *C07D 319/06* (2013.01); *C08F 34/02* (2013.01)

(58) Field of Classification Search
  CPC ...... C08F 224/00; C08F 34/02; C07D 317/00; C07D 317/42; C07D 319/06
  See application file for complete search history.

(56) References Cited

U.S. PATENT DOCUMENTS

| | | | |
|---|---|---|---|
| 3,308,107 | A | 3/1967 | Selman et al. |
| 3,978,030 | A | 8/1976 | Resnick |
| 4,485,250 | A | 11/1984 | Squire |
| 4,754,009 | A | 6/1988 | Squire |
| 4,897,457 | A | 1/1990 | Nakamura et al. |
| 5,324,889 | A | 6/1994 | Resnick |
| 5,326,839 | A | 7/1994 | Resnick |
| 5,408,020 | A | 4/1995 | Hung et al. |
| 6,469,185 | B1 | 10/2002 | Russo et al. |
| 8,017,709 | B2 | 9/2011 | Otozawa et al. |
| 8,828,121 | B1 | 9/2014 | He et al. |
| 9,643,124 | B2 | 5/2017 | Zhang et al. |
| 2011/0027687 | A1 | 2/2011 | Hommura et al. |
| 2016/0045859 | A1 | 2/2016 | Zhang et al. |

FOREIGN PATENT DOCUMENTS

| | | | | |
|---|---|---|---|---|
| CN | 101356230 A1 | 1/2008 | | |
| CN | 108517025 A | * 9/2018 | ........... | C07D 319/06 |

(Continued)

OTHER PUBLICATIONS

Machine translation of CN 108047189 (no date).

(Continued)

*Primary Examiner* — Amanda C. Walke
(74) *Attorney, Agent, or Firm* — Procopio, Cory, Hargreaves & Savitch LLP

(57) ABSTRACT

Provided herein are perfluoro copolymers of a perfluoro dioxole monomer, a perfluoro dioxane monomer, and an optional perhalo monomer. Methods of making the perfluoro copolymers and methods of using the perfluoro copolymers are also disclosed.

20 Claims, 3 Drawing Sheets

(56) References Cited

FOREIGN PATENT DOCUMENTS

| | | |
|---|---|---|
| EP | 0633257 B1 | 4/1997 |
| WO | 2019165636 A1 | 9/2019 |

OTHER PUBLICATIONS

Invitation to pay additional fees, dated Apr. 28, 2023.
National Center for Biotechnology Information (2023). PubChem Compound Summary for CID 20205669, 2-(Difluoromethylidene)-4,4,5,5,6-pentafluoro-6-(trifluoromethyl)-1,3-dioxane. Retrieved Apr. 14, 2023, 9 pgs. [online] https://pubchem.ncbi.nlm.nih.gov/compound/20205669.
International Search Report and Written Opinion for PCT App No. PCT/US2023/014395 dated Jun. 26, 2023, 9 pgs.

\* cited by examiner

PERFLUORO COPOLYMERS

CROSS-REFERENCE TO RELATED APPLICATIONS

This application is a continuation to U.S. patent application Ser. No. 17/741,391, filed on May 10, 2022, which is hereby incorporated herein by reference as if set forth in full.

SUMMARY OF THE DISCLOSURE

One aspect of the present disclosure relates to a perfluoro copolymer of a first monomer, a second monomer, and an optional third monomer, wherein the first monomer is a perfluoro dioxole compound, wherein the second monomer is a perfluoro dioxane compound of Formula I:

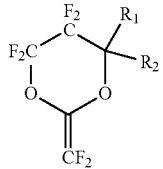

Formula I wherein the $R_1$ and $R_2$ are each independently F or a C1-C4 perfluoro alkyl, provided that R1 and R2 are not the same, and wherein the third monomer is selected from: (a) a perhaloolefin wherein each halogen is fluorine or chlorine, provided that at least one half of the halogen atoms must be fluorine, or (b) a perfluoro(alkyl vinyl ether).

In some embodiments, the first monomer is selected from perfluoro-2,2-dimethyl-1,3-dioxole, perfluoro-2-fluoro-2-methyl-1,3-dioxole, or perfluoro-1,3-dioxole. In some embodiments, the first monomer is perfluoro-2,2-dimethyl-1,3-dioxole.

In some embodiments, $R_1$ in the second monomer is F. In some embodiments, $R_2$ in the second monomer is $CF_3$.

In some embodiments, the first monomer is present at no less than about 30 mole percent, preferably at no less than about 40 mole percent, of total moles of all monomers. In some embodiments, the first monomer is present at no less than about 45 mole percent of total moles of all monomers. In some embodiments, the first monomer is present at no less than about 50 mole percent of total moles of all monomers. In some embodiments, the first monomer is present at no less than about 55 mole percent of total moles of all monomers. In some embodiments, the first monomer is present at no less than about 60 mole percent of total moles of all monomers. In some embodiments, the first monomer is present at no less than about 65 mole percent of total moles of all monomers. In some embodiments, the first monomer is present at no less than about 70 mole percent of total moles of all monomers. In some embodiments, the first monomer is present at no less than about 75 mole percent of total moles of all monomers. In some embodiments, the first monomer is present at no less than about 80 mole percent of total moles of all monomers. In some embodiments, the first monomer is present at no less than about 85 mole percent of total moles of all monomers. In some embodiments, the first monomer is present at no less than about 90 mole percent of total moles of all monomers. In some embodiments, the first monomer is present at no less than about 95 mole percent of total moles of all monomers.

In some embodiments, the second monomer is present at no more than about 70 mole percent, preferably no more than about 60 mole percent, more preferably no more than about 40 mole percent, and most preferably no more than about 30 mole percent, of total moles of all monomers. In some embodiments, the second monomer is present at no more than about 25 mole percent of total moles of all monomers. In some embodiments, the second monomer is present at no more than about 20 mole percent of total moles of all monomers. In some embodiments, the second monomer is present at no more than about 15 mole percent of total moles of all monomers. In some embodiments, the second monomer is present at no more than about 10 mole percent of total moles of all monomers. In some embodiments, the second monomer is present at no more than about 5 mole percent of total moles of all monomers.

In some embodiments, the third monomer is a perhaloolefin. In some embodiment, the perhaloolefin is selected from: tetrafluoroethylene or chlorotrifluoroethylene. In some embodiments, the third monomer is a perfluoro vinylether. In some embodiment, the perfluoro vinylether is perfluoro methyl vinylether.

In some embodiments, the third monomer is present at no more than about 40 mole percent based on total moles of all monomers. In some embodiments, the third monomer is present at no more than about 35 mole percent based on total moles of all monomers. In some embodiments, the third monomer is present at no more than about 30 mole percent based on total moles of all monomers. In some embodiments, the third monomer is present at no more than about 25 mole percent based on total moles of all monomers. In some embodiments, the third monomer is present at no more than about 20 mole percent based on total moles of all monomers. In some embodiments, the third monomer is present at no more than about 15 mole percent based on total moles of all monomers. In some embodiments, the third monomer is present at no more than about 10 mole percent based on total moles of all monomers. In some embodiments, the third monomer is present at no more than about 5 mole percent based on total moles of all monomers.

In some embodiments, the third monomer is not present.

In some embodiments, the perfluoro copolymer is essentially free of additional monomers that are not one of the first, second, and third monomers.

In some embodiments, the perfluoro copolymer disclosed herein is amorphous.

In some embodiments, the perfluoro copolymer has a Tg of at least about 140° C. In some embodiments, the perfluoro copolymer has a Tg of at least about 150° C. In some embodiments, the perfluoro copolymer has a Tg of at least about 160° C. In some embodiments, the perfluoro copolymer has a Tg of at least about 170° C. In some embodiments, the perfluoro copolymer has a Tg of at least about 180° C. In some embodiments, the perfluoro copolymer has a Tg of at least about 200° C. In some embodiments, the perfluoro copolymer has a Tg of at least about 230° C. In some embodiments, the perfluoro copolymer has a Tg of at least about 240° C. In some embodiments, the perfluoro copolymer has a Tg of no more than about 250° C. In some embodiments, the perfluoro copolymer has a Tg of no more than about 260° C. In some embodiments, the perfluoro copolymer has a Tg of no more than about 270° C. In some embodiments, the perfluoro copolymer has a Tg of no more than about 280° C. In some embodiments, the perfluoro copolymer has a Tg of no more than about 290° C. In some embodiments, the perfluoro copolymer has a Tg of no more than about 300° C. In some embodiments, the perfluoro copolymer has a Tg of no more than about 310° C. In some embodiments, the perfluoro copolymer has a Tg of no more than about 320° C. In some embodiments, the perfluoro copolymer has a Tg of no more than about 320° C.

In some embodiments, the perfluoro copolymer has an FC-75 solubility of up to about 10 wt %. In some embodiments, the perfluoro copolymer has an FC-75 solubility of up to about 8 wt %. In some embodiments, the perfluoro copolymer has an FC-75 solubility of up to about 6 wt %. In some embodiments, the perfluoro copolymer has an FC-75 solubility of up to about 5 wt %. In some embodiments, the perfluoro copolymer has an FC-75 solubility of up to about 4 wt %. In some embodiments, perfluoro copolymer has an FC-75 solubility of up to about 3 wt %. In some embodiments, the perfluoro copolymer has an FC-75 solubility of up to about 2 wt %.

In some embodiments, the perfluoro copolymer has an FC-40 solubility of up to about 2 wt %. In some embodiments, the perfluoro copolymer has an FC-40 solubility of up to about 1 Wt %.

In some embodiments, the perfluoro copolymer is stable up to about 420° C. In some embodiments, the perfluoro copolymer is stable up to about 430° C. In some embodiments, the perfluoro copolymer is stable up to about 440° C. In some embodiments, the perfluoro copolymer is stable up to about 450° C. In some embodiments, the perfluoro copolymer is stable up to about 460° C. In some embodiments, the perfluoro copolymer is stable up to about 470° C.

In some embodiments, the perfluoro copolymer can be processed at a temperature of up to about 420° C. In some embodiments, the perfluoro copolymer can be processed at a temperature of up to about 410° C. In some embodiments, the perfluoro copolymer can be processed at a temperature of up to about 400° C. In some embodiments, the perfluoro copolymer can be processed at a temperature of up to about 380° C.

In some embodiments, the perfluoro copolymer has an $O_2$ permeance of at least 4200 GPU. In some embodiments, the perfluoro copolymer has an $O_2$ permeance of at least 4400 GPU. In some embodiments, the perfluoro copolymer has an $O_2$ permeance of at least 4600 GPU. In some embodiments, the perfluoro copolymer has an $O_2$ permeance of at least 4800 GPU. In some embodiments, the perfluoro copolymer has an $O_2$ permeance of at least 5000 GPU.

In some embodiments, the perfluoro copolymer has an $N_2$ permeance of at least 2100 GPU. In some embodiments, the perfluoro copolymer has an $N_2$ permeance of at least 2200 GPU. In some embodiments, the perfluoro copolymer has an $N_2$ permeance of at least 2300 GPU. In some embodiments, the perfluoro copolymer has an $N_2$ permeance of at least 2400 GPU. In some embodiments, the perfluoro copolymer has an $N_2$ permeance of at least 2500 GPU.

In some embodiments, the perfluoro copolymer has an $H_2$ permeance of at least 8000 GPU. In some embodiments, the perfluoro copolymer has an $H_2$ permeance of at least 8500 GPU. In some embodiments, the perfluoro copolymer has an $H_2$ permeance of at least 9000 GPU. In some embodiments, the perfluoro copolymer has an $H_2$ permeance of at least 9500 GPU. In some embodiments, the perfluoro copolymer has an $H_2$ permeance of at least 10000 GPU.

In some embodiments, the first monomer is perfluoro-2,2-dimethyl-1,3-dioxole; the second monomer is perfluoro-2-methylene-4-methyl-1,3-dioxane; and the third copolymer is not present. In some embodiments, the first monomer is perfluoro-2,2-dimethyl-1,3-dioxole; the second monomer is perfluoro-2-methylene-4-methyl-1,3-dioxane; and the perfluoro copolymer is essentially free of additional monomers that are not one of the first and second monomers.

Another aspect of the present disclosure relates to a method of making a perfluoro copolymer disclosed herein, the method comprising: mixing the first monomer, the second monomer, the optional third monomer, and an initiator in a reaction medium to form a polymerization mixture; and initiating polymerization to form the perfluoro copolymer.

In some embodiments, the reaction medium comprises one or more fluorinated solvents.

In some embodiments, the one or more fluorinated solvents are selected from Opteon SF79, perfluorooctanoic acid, Vertrel XF, or combinations thereof. The method of claim 89-91, wherein the reaction medium is a solution.

In some embodiments, the reaction medium further comprises water. In some embodiments, the reaction medium is an emulsion.

In some embodiments, the initiator is a free radical initiator. In some embodiments, the initiator is a peroxide initiator. In some embodiments, the initiator is an organic peroxide initiator. In some embodiments, the initiator is selected from perfluoropropionyl peroxide, 4, 4'-bis(t-butylcyclohexyl)peroxy decarbonate, or $(NH4)_2S_2O_8$.

In some embodiments, the polymerization is initiated by heating the polymerization mixture.

In some embodiments, the polymerization mixture is heated at a temperature of from about 50° C. to about 80° C. In some embodiments, the polymerization mixture is heated at a temperature of from about 60° C. to about 75° C.

In some embodiments, the polymerization mixture is heated at a temperature of from about 50° C. to about 80° C. until the perfluoro copolymer is formed. In some embodiments, the polymerization mixture is heated at a temperature of from about 60° C. to about 75° C. until the perfluoro copolymer is formed.

In some embodiments, the polymerization mixture is heated at a temperature of from about 50° C. to about 80° C. until the polymerization is completed. In some embodiments, the polymerization mixture is heated at a temperature of from about 60° C. to about 75° C. until the polymerization is completed.

In some embodiments, the polymerization mixture is heated for a period of from about 4 h to about 24 h. In some embodiments, the polymerization mixture is heated for a period of from about 6 h to about 12 h. In some embodiments, the polymerization mixture is contacted with fluorine gas after completion of polymerization.

In some embodiments, the method further comprises separating the perfluoro copolymer from the polymerization mixture. In some embodiments, the perfluoro copolymer is separated from the polymerization mixture by removing volatile components of the polymerization mixture through evaporation. In some embodiments, the perfluoro copolymer is separated from the polymerization mixture by adding an anti-solvent to the polymerization mixture to precipitate the perfluoro copolymer. In some embodiments, the anti-solvent is nitric acid.

Another aspect of the present disclosure relates to an article of manufacturing, comprising the perfluoro copolymer disclosed herein. In some embodiments, the article of manufacturing is a film formed with the perfluoro copolymer. In some embodiments, the film is a free-standing film.

Another aspect of the present disclosure relates to a perfluoro dioxane compound of Formula I:

Formula I

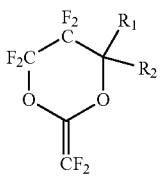

wherein the $R_1$ and $R_2$ are each independently F or a C1-C4 perfluoro alkyl, provided that R1 and R2 are not the same.

In some embodiments, $R_1$ is F. In some embodiments, $R_2$ is $CF_3$. In some embodiments, the perfluoro compound of Formula I is in neat liquid form.

Another aspect of the present disclosure relates to a perfluoro dioxane compound of Formula II:

Formula II

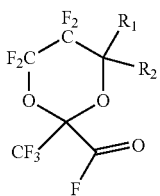

wherein the $R_1$ and $R_2$ are each independently F or a C1-C4 perfluoro alkyl, provided that R1 and R2 are not the same.

In some embodiments, $R_1$ is F. In some embodiments, $R_2$ is $CF_3$. In some embodiments, the perfluoro compound of Formula II is in neat liquid form.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE DISCLOSURE

Figure 1:
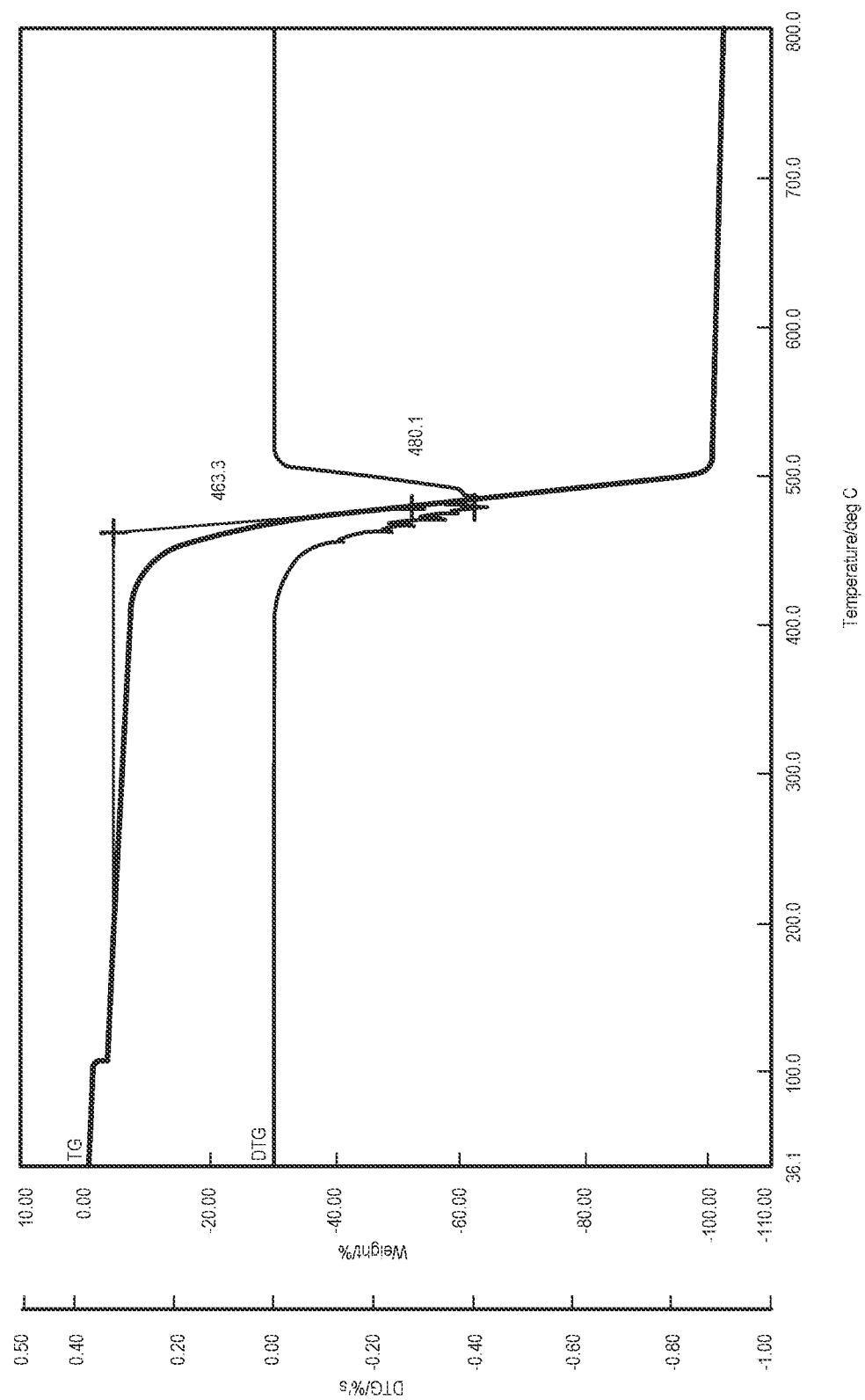
FIG. 1 illustrates TGA analysis results of a perfluoro copolymer according to a non-limiting embodiment.

Provided herein, in some embodiments, are perfluoro copolymer with one or more improved characteristic over homopolymers of the monomers. In some embodiments, those characteristics are one or combination of lower crystallinity (e.g., amorphous), more desirable Tg, better solubility in fluorinated solvents, better thermostability, better processability, higher gas permeance, and better gas permeation selectivity. Also provided herein, in some embodiment, are methods of making the perfluoro copolymers. Further provided herein, in some embodiment, are method of using the perfluoro copolymers to make an article of manufacture, such as a gas permeating film. Further provided herein, in some embodiments, are perfluoro dioxane monomers and method of making thereof.

Perfluoro Dioxole Monomer

Perfluoro dioxole monomers, such as perfluoro-2,2-dimethyl-1,3-dioxole (PDD) can be polymerized to form homopolymers. PDD has the following formula:

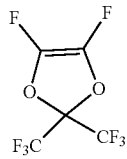

The PDD homopolymer, has a high glass transition temperature of about 335° C. The present disclosure recognizes that PDD homopolymers can be brittle, have poor melt flow and/or have low solubility in fluorinated solvents, among other features, which make it difficult to process into final products under certain circumstance.

Other perfluoro dioxole monomers include perfluoro-1,3-dioxole and perfluoro-2-fluoro-2-methyl-1,3-dioxole. Their chemical structures are provided below:

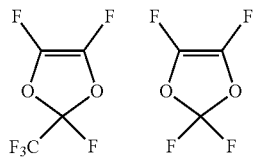

According to one aspect of the present disclosure, a perfluoro dioxole monomer (e.g., PDD), when copolymerized with a perfluoro dioxane monomer and optionally with another perhalo monomer (e.g., perhaloolefin or perfluoro vinylether), form a perfluoro copolymer with one or more improved characteristics including, but not limited to, lower crystallinity (e.g., amorphous), more desirable Tg, better solubility in fluorinated solvents, better thermostability, better processability, higher gas permeance, better gas permeation selectivity, or combinations thereof.

Perfluoro Dioxane Monomer

Another aspect of the present disclosure relates to a perfluoro dioxane monomer that polymerizes with a perfluoro dioxole monomer, such as PDD, and another optional perfluoro compound to form perfluoro copolymers. In some embodiments, the perfluoro dioxane monomer has a structure of Formula I:

Formula I

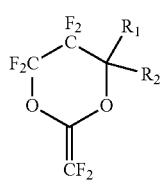

wherein the $R_1$ and $R_2$ are each independently F or a C1-C4 perfluoro alkyl, provided that R1 and R2 are not the same.

In some embodiments, $R_1$ is F. In some embodiments, $R_2$ is $CF_3$. In some embodiments, the perfluoro compound of Formula I is in neat liquid form.

The perfluoro dioxane monomers of Formula I can be prepared from perfluoro dioxane compounds of Formula II:

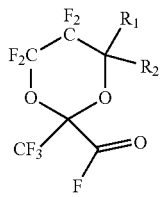

Formula II wherein the $R_1$ and $R_2$ are each independently F or a C1-C4 perfluoro alkyl, provided that R1 and R2 are not the same.

In some embodiments, $R_1$ is F. In some embodiments, $R_2$ is $CF_3$. In some embodiments, the perfluoro compound of Formula II is in neat liquid form.

The synthetic strategy of the perfluoro dioxane monomers disclosed herein is provided below using perfluoro-2-methylene-4-methyl-1,3-dioxane (PMX) as a non-limiting example:

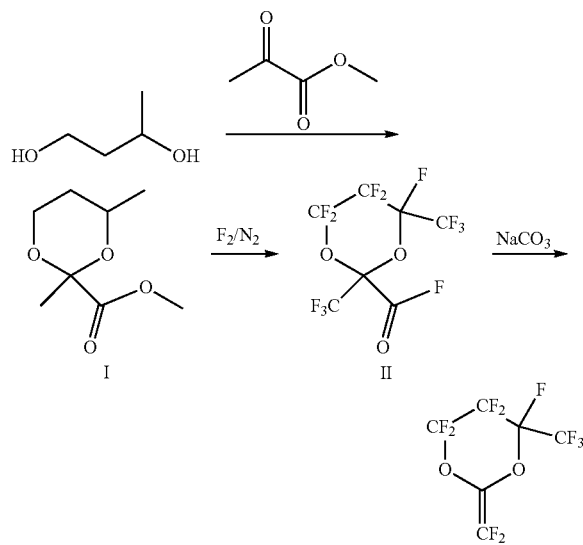

Starting from the condensation between 1,3-butanediol and methyl pyruvate, the dioxane hydrocarbon precursor (I) is obtained. It is fluorinated and transformed to perfluoro fluoride intermediate (II). PMX is prepared by contacting gaseous II with an anhydrous alkali or alkaline earth metal oxygen-containing salt at a temperature of about 200° C. to 400° C.

According to one aspect of the present disclosure, a perfluoro dioxane monomer (e.g., PMX), when copolymerized with a perfluoro dioxole monomer (e.g., PDD), and optionally with another perhalo monomer (e.g., perhaloolefin or perfluoro vinylether), form a perfluoro copolymer with one or more improved characteristics including, but not limited to, lower crystallinity (e.g., amorphous), more desirable Tg, better solubility in fluorinated solvents, better thermostability, better processability, higher gas permeance, better gas permeation selectivity, or combinations thereof.

Optional Perhalo Monomer

According to some embodiments of the present disclosure, an optional monomer can be used with the perfluoro dioxole monomer and perfluoro dioxane monomer to form the perfluoro copolymer. In some embodiment, the optional monomer is a perhaloolefin such as tetrafluoroethylene or chlorotrifluoroethylene. In some embodiments, the optional monomer is a perfluoro vinylether, such as perfluoro methyl vinyl ether.

Tetrafluoroethylene (TFE) is a fluorocarbon with the chemical formula C2F4. It is the simplest perfluorinated alkene. This gaseous species is used primarily in the industrial preparation of fluoropolymers. Polymerization of tetrafluoroethylene produces polytetrafluoroethylene (PTFE) polymers such as TEFLON™ and FLUON™. PTFE is one of the two fluorocarbon resins composed wholly of fluorine and carbon. The other resin composed purely of carbon and fluorine is the copolymer of TFE with typically 6-9% hexafluoropropene (HFP), which is known as FEP (fluorinated ethylene propylene copolymer). TFE is also used in the preparation of numerous copolymers that also include hydrogen and/or oxygen, including both fluoroplastics and fluoroelastomers. Typical TFE-based fluoroplastics include ETFE, the alternating 1:1 copolymer with ethylene, and PFA, which is a random copolymer similar to FEP but with a minor amount of a perfluoroalkyl vinyl ether (PAVE) rather than HFP. DuPont uses primarily perfluoro(methylvinylether), whereas Daikin uses primarily perfluoro(propylvinylether) in manufacturing PFA. There are numerous other fluoropolymers that contain tetrafluoroethylene, but usually not at greater than 50% by weight.

Chlorotrifluoroethylene (CTFE) is a chlorofluorocarbon with chemical formula $CFCl=CF_2$. It is commonly used as a refrigerant in cryogenic applications. CTFE has a carbon-carbon double bond and so can be polymerized to form polychlorotrifluoroethylene or copolymerized to produce the plastic ECTFE. PCTFE has the trade name NEOFLON PCTFE from Daikin Industries in Japan, and used to be produced under the trade name KEL-F from 3M Corporation in Minnesota.

As a special fluorine-containing monomer, perfluorinated vinyl methyl ether (PMVE) is widely applied in fluoroplastics and fluorine rubber. It can copolymerize with tetrafluoroethylene to form perfluorinated ether elastomer with properties of high temperature and strong chemical corrosion resistance. It can copolymerize with tetrafluoroethylene and vinylidene fluoride to form polyvinylidene fluoride ether rubber, peroxide cross-linked available, with excellent performance at low temperature. It can copolymerize with tetrafluoroethylene to form fluorine resin for melt processing; It is important raw material to synthesize new pesticides and benzene fluorouracil.

Perfluoro Copolymers

In some embodiments, the present disclosure relates to a perfluoro copolymer of a first monomer, a second monomer, and an optional third monomer, wherein the first monomer is a perfluoro dioxole compound, wherein the second monomer is a perfluoro compound of Formula Formula I

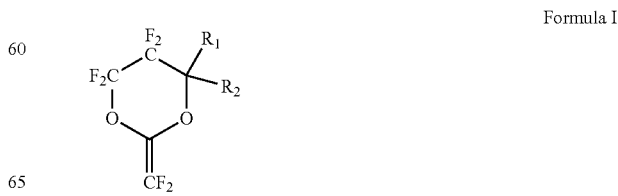

wherein the $R_1$ and $R_2$ are each independently F or a C1-C4 perfluoro alkyl, provided that R1 and R2 are not the same, and wherein the third monomer is selected from: (a) a perhaloolefin wherein each halogen is fluorine or chlorine, provided that at least one half of the halogen atoms must be fluorine, or (b) a perfluoro(alkyl vinyl ether), provide that the third monomer, if present, is different from the first monomer.

In some embodiments, the first monomer is selected from perfluoro-2,2-dimethyl-1,3-dioxole, perfluoro-2-fluoro-2-methyl-1,3-dioxole, or perfluoro-1,3-dioxole. In some embodiments, the first monomer is perfluoro-2,2-dimethyl-1,3-dioxole.

In some embodiments, $R_1$ in the second monomer is F. In some embodiments, $R_2$ in the second monomer is $CF_3$.

In some embodiments, the first monomer is present at no less than about 40 mole percent of total moles of all monomers. In some embodiments, the first monomer is present at no less than about 45 mole percent of total moles of all monomers. In some embodiments, the first monomer is present at no less than about 50 mole percent of total moles of all monomers. In some embodiments, the first monomer is present at no less than about 55 mole percent of total moles of all monomers. In some embodiments, the first monomer is present at no less than about 60 mole percent of total moles of all monomers. In some embodiments, the first monomer is present at no less than about 65 mole percent of total moles of all monomers. In some embodiments, the first monomer is present at no less than about 70 mole percent of total moles of all monomers. In some embodiments, the first monomer is present at no less than about 75 mole percent of total moles of all monomers. In some embodiments, the first monomer is present at no less than about 80 mole percent of total moles of all monomers. In some embodiments, the first monomer is present at no less than about 85 mole percent of total moles of all monomers. In some embodiments, the first monomer is present at no less than about 90 mole percent of total moles of all monomers. In some embodiments, the first monomer is present at no less than about 95 mole percent of total moles of all monomers.

In some embodiments, the second monomer is present at no more than about 30 mole percent of total moles of all monomers. In some embodiments, the second monomer is present at no more than about 25 mole percent of total moles of all monomers. In some embodiments, the second monomer is present at no more than about 20 mole percent of total moles of all monomers. In some embodiments, the second monomer is present at no more than about 15 mole percent of total moles of all monomers. In some embodiments, the second monomer is present at no more than about 10 mole percent of total moles of all monomers. In some embodiments, the second monomer is present at no more than about 5 mole percent of total moles of all monomers.

In some embodiments, the first monomer is perfluoro-2,2-dimethyl-1,3-dioxole; the second monomer is perfluoro-2-methylene-4-methyl-1,3-dioxane; and the third copolymer is not present. In some embodiments, the first monomer is perfluoro-2,2-dimethyl-1,3-dioxole; the second monomer is perfluoro-2-methylene-4-methyl-1,3-dioxane; and the perfluoro copolymer is essentially free of additional monomers that are not one of the first and second monomers.

In some embodiments, the optional third monomer is a perhaloolefin selected from: perhaloolefin selected from tetrafluoroethylene or chlorotrifluoroethylene. In some embodiments, the third monomer is perfluoro(methyl vinyl ether).

In some embodiments, the third monomer is present at no more than about 40 mole percent based on total moles of all monomers. In some embodiments, the third monomer is present at no more than about 35 mole percent based on total moles of all monomers. In some embodiments, the third monomer is present at no more than about 30 mole percent based on total moles of all monomers. In some embodiments, the third monomer is present at no more than about 25 mole percent based on total moles of all monomers. In some embodiments, the third monomer is present at no more than about 20 mole percent based on total moles of all monomers. In some embodiments, the third monomer is present at no more than about 15 mole percent based on total moles of all monomers. In some embodiments, the third monomer is present at no more than about 10 mole percent based on total moles of all monomers. In some embodiments, the third monomer is present at no more than about 5 mole percent based on total moles of all monomers.

In some embodiments, the third monomer is not present.

In some embodiments, the perfluoro copolymer is essentially free of additional monomers that are not one of the first, second, and third monomers.

In some embodiment, the perfluoro copolymers is made from monomers that are perhalogenated instead of perfluorinated, such as when the third monomer is chlorotrifluoroethylene. In such embodiments, the term "perfluoro copolymer" encompasses copolymers in which at least 80% of H is substituted with F, preferably in which at least 90% of H is substituted with F.

According to one aspect of the present disclosure, a perfluoro dioxane monomer (e.g., PMX), when copolymerized with a perfluoro dioxole monomer (e.g., PDD), and optionally with another perhalo monomer (e.g., perhaloolefin or perfluoro vinylether), form a perfluoro copolymer with one or more improved characteristics including, but not limited to, lower crystallinity (e.g., amorphous), more desirable Tg, better solubility in fluorinated solvents, better thermostability, better processability, higher gas permeance, better gas permeation selectivity, or combinations thereof.

Crystallinity/Amorphousness

The presence and or quantification of the crystallinity or lack thereof (amorphousness) can be determined from a number of characterization methods known in the art, but not limited to, XRPD, vibrational spectroscopy (FTIR, NIR, Raman), polarized optical microscopy, calorimetry, thermal analysis and solid-state NMR.

X-Ray Diffraction to Determine Crystallinity/Amorphousness

XRPD analyses are performed using an X-ray powder diffractometer (for example, a Bruker D8 Advance X-ray diffractometer) using Cu Kα radiation. Diffractograms are typically collected between 2 and 40 degrees 2 theta. Where required low background XRPD sample holders are employed to minimize background noise.

The diffractograms of the deposited active agent are compared with diffractograms of known crystallized active agents, for example micronized crystalline sirolimus in powder form. XRPD patterns of crystalline forms show strong diffraction peaks whereas amorphous show diffuse and non-distinct patterns. Crystallinity is shown in arbitrary Intensity units.

A related analytical technique which may also be used to provide crystallinity detection is wide angle scattering of radiation for which the technique and variations of the technique specific to a particular sample would be obvious to one of skill in the art.

Differential Scanning Calorimetry (DSC)

DSC can provide qualitative evidence of the crystallinity of the copolymer using standard DSC techniques obvious to one of skilled in the art. Low-crystallinity, or amorphousness, in some embodiments, can be shown using this analytical method. The heat of fusion decreases with the percent crystallinity. Thus, the degree of crystallinity could be determined relative to a pure sample, or versus a calibration curve created from a sample of amorphous drug spiked and tested by DSC with known amounts of crystalline polymer.

In some embodiments, the perfluoro copolymer of the present disclosure has a crystallinity lower than a homopolymer of the perfluoro dioxole monomer. In some embodiment, the perfluoro copolymer of the present disclosure has a crystallinity lower than a homopolymer of the optional perhalo monomer. the perfluoro copolymer of the present disclosure has a crystallinity lower than both a homopolymer of the perfluoro dioxole monomer and a homopolymer of the optional perhalo monomer.

In some embodiments, the less than 15% of the perfluoro copolymer disclosed herein is crystalline. In some embodiments, the less than 15% of the perfluoro copolymer disclosed herein is crystalline. In some embodiments, the less than 10% of the perfluoro copolymer disclosed herein is crystalline. In some embodiments, the less than 9% of the perfluoro copolymer disclosed herein is crystalline. In some embodiments, the less than 8% of the perfluoro copolymer disclosed herein is crystalline. In some embodiments, the less than 7% of the perfluoro copolymer disclosed herein is crystalline. In some embodiments, the less than 6% of the perfluoro copolymer disclosed herein is crystalline. In some embodiments, the less than 5% of the perfluoro copolymer disclosed herein is crystalline. In some embodiments, the less than 4% of the perfluoro copolymer disclosed herein is crystalline. In some embodiments, the less than 3% of the perfluoro copolymer disclosed herein is crystalline. In some embodiments, the less than 2% of the perfluoro copolymer disclosed herein is crystalline. In some embodiments, the less than 1% of the perfluoro copolymer disclosed herein is crystalline. In some embodiments, the less than 0.5% of the perfluoro copolymer disclosed herein is crystalline. In some embodiments, the less than 0.1% of the perfluoro copolymer disclosed herein is crystalline. In some embodiments, the less than 0.01% of the perfluoro copolymer disclosed herein is crystalline. In some embodiments, the perfluoro copolymer disclosed herein is amorphous.

Glass Transition Temperature

The glass transition of a liquid to a solid-like state may occur with either cooling or compression. Below the transition temperature range, the glassy structure does not relax in accordance with the cooling rate used. The expansion coefficient for the glassy state is roughly equivalent to that of the crystalline solid. If slower cooling rates are used, the increased time for structural relaxation (or intermolecular rearrangement) to occur may result in a higher density glass product. Similarly, by annealing (and thus allowing for slow structural relaxation) the glass structure in time approaches an equilibrium density corresponding to the supercooled liquid at this same temperature. Tg is located at the intersection between the cooling curve (volume versus temperature) for the glassy state and the supercooled liquid.

The configuration of the glass in this temperature range changes slowly with time towards the equilibrium structure. The principle of the minimization of the Gibbs free energy provides the thermodynamic driving force necessary for the eventual change. At somewhat higher temperatures than Tg, the structure corresponding to equilibrium at any temperature is achieved quite rapidly. In contrast, at considerably lower temperatures, the configuration of the glass remains sensibly stable over increasingly extended periods of time.

In polymers the glass transition temperature, Tg, is often expressed as the temperature at which the Gibbs free energy is such that the activation energy for the cooperative movement of 50 or so elements of the polymer is exceeded. This allows molecular chains to slide past each other when a force is applied. From this definition, we can see that the introduction of relatively stiff chemical groups (such as benzene rings) will interfere with the flowing process and hence increase Tg. The stiffness of thermoplastics decreases due to this effect. When the glass temperature has been reached, the stiffness stays the same for a while, i.e., at or near E2, until the temperature exceeds Tm, and the material melts. This region is called the rubber plateau.

Coming from the low-temperature side, the shear modulus drops by many orders of magnitude at the glass transition temperature Tg. A molecular-level mathematical relation for the temperature-dependent shear modulus of the polymer glass on approaching Tg from below has been developed by Alessio Zaccone and Eugene Terentjev. Even though the shear modulus does not really drop to zero (it drops down to the much lower value of the rubber plateau), upon setting the shear modulus to zero in the Zaccone-Terentjev formula, an expression for Tg is obtained which recovers the Flory-Fox equation, and also shows that Tg is inversely proportional to the thermal expansion coefficient in the glass state. This procedure provides yet another operational protocol to define the Tg of polymer glasses by identifying it with the temperature at which the shear modulus drops by many orders of magnitude down to the rubbery plateau. One frequently used definition of Tg uses the energy release on heating in differential scanning calorimetry.

In some embodiments, the perfluoro copolymer has a Tg of at least about 140° C. In some embodiments, the perfluoro copolymer has a Tg of at least about 150° C. In some embodiments, the perfluoro copolymer has a Tg of at least about 160° C. In some embodiments, the perfluoro copolymer has a Tg of at least about 170° C. In some embodiments, the perfluoro copolymer has a Tg of at least about 180° C. In some embodiments, the perfluoro copolymer has a Tg of at least about 200° C. In some embodiments, the perfluoro copolymer has a Tg of at least about 230° C. In some embodiments, the perfluoro copolymer has a Tg of at least about 240° C. In some embodiments, the perfluoro copolymer has a Tg of no more than about 250° C. In some embodiments, the perfluoro copolymer has a Tg of no more than about 260° C. In some embodiments, the perfluoro copolymer has a Tg of no more than about 270° C. In some embodiments, the perfluoro copolymer has a Tg of no more than about 280° C. In some embodiments, the perfluoro copolymer has a Tg of no more than about 290° C. In some embodiments, the perfluoro copolymer has a Tg of no more than about 300° C. In some embodiments, the perfluoro copolymer has a Tg of no more than about 310° C. In some embodiments, the perfluoro copolymer has a Tg of no more than about 320° C. In some embodiments, the perfluoro copolymer has a Tg of no more than about 320° C.

Solubility in Fluorinated Solvents

FC-40, commercially available from 3M, is a perfluoro alkyl amine. FC-40 is non-conductive, thermally and chemically stable fluid ideal for single phase heat transfer fluid applications, especially in the electronics and semiconductor industry for testers, CVD and TFT manufacturing. Its wide liquid range (−57 to 165 deg C.) and compatibility makes it well suited for a variety of electronic single and two phase heat transfer applications, including in the semiconductor market for etchers, ion implanters, testers, CVD and TFT manufacturing. Because FC-40 has a narrow boiling range, its composition will change little with time, this keeps fluid loss to a minimum and insures consistent transport properties.

FC-75, commercially available from 3M, is a fluorocarbon derivative of tetrahydrofuran with the chemical formula $C_8F_{16}O$. Its chemical structure corresponds to Perfluoro (butyltetrahydrofuran). It is practically insoluble in water. It is used as an inert coolant fluid in electronics and other applications, and as a solvent.

In some embodiments, the perfluoro copolymer has an FC-75 solubility of up to about 10 wt %. In some embodiments, the perfluoro copolymer has an FC-75 solubility of up to about 8 wt %. In some embodiments, the perfluoro copolymer has an FC-75 solubility of up to about 6 wt %. In some embodiments, the perfluoro copolymer has an FC-75 solubility of up to about 5 wt %. In some embodiments, the perfluoro copolymer has an FC-75 solubility of up to about 4 wt %. In some embodiments, perfluoro copolymer has an FC-75 solubility of up to about 3 wt %. In some embodiments, the perfluoro copolymer has an FC-75 solubility of up to about 2 wt %.

In some embodiments, the perfluoro copolymer has an FC-40 solubility of up to about 2 wt %. In some embodiments, the perfluoro copolymer has an FC-40 solubility of up to about 1 Wt %.

Thermostability

Thermal stability of polymer is defined as the ability of the polymeric material to resist the action of heat and to maintain its properties, such as strength, toughness, or elasticity at given temperature. The thermal stability of polymers is usually determined by thermogravimetric analysis (TGA). The weight loss, as a function of temperature, is monitored and some characteristic temperatures as Tx % (where x is a mass loss, e.g., x=1%, 3%, 5%, 10%, 20%, 50%) are determined from the thermogravimetric (TG) profile. Thermal stability of polymer depends factors including its chemical structure, degree of crystallinity, and molecular weight. For example, aromatic structures in the polymer backbone and cross-linking processes can improve the thermal stability of polymers. On the other hand, double bonds or oxygen-containing structures in the main chain can make polymers less resistant to high temperatures.

In some embodiments, the perfluoro copolymer is stable (less than 50% weight loss) up to about 420° C. In some embodiments, the perfluoro copolymer is stable (less than 50% weight loss) up to about 430° C. In some embodiments, the perfluoro copolymer is stable (less than 50% weight loss) up to about 440° C. In some embodiments, the perfluoro copolymer is stable (less than 50% weight loss) up to about 450° C. In some embodiments, the perfluoro copolymer is stable (less than 50% weight loss) up to about 460° C. In some embodiments, the perfluoro copolymer is stable (less than 50% weight loss) up to about 470° C.

In some embodiments, the perfluoro copolymer is stable (less than 20% weight loss) up to about 420° C. In some embodiments, the perfluoro copolymer is stable (less than 20% weight loss) up to about 430° C. In some embodiments, the perfluoro copolymer is stable (less than 20% weight loss) up to about 440° C. In some embodiments, the perfluoro copolymer is stable (less than 20% weight loss) up to about 450° C. In some embodiments, the perfluoro copolymer is stable (less than 20% weight loss) up to about 460° C. In some embodiments, the perfluoro copolymer is stable (less than 20% weight loss) up to about 470° C.

In some embodiments, the perfluoro copolymer is stable (less than 10% weight loss) up to about 420° C. In some embodiments, the perfluoro copolymer is stable (less than 10% weight loss) up to about 430° C. In some embodiments, the perfluoro copolymer is stable (less than 10% weight loss) up to about 440° C. In some embodiments, the perfluoro copolymer is stable (less than 10% weight loss) up to about 450° C. In some embodiments, the perfluoro copolymer is stable (less than 10% weight loss) up to about 460° C. In some embodiments, the perfluoro copolymer is stable (less than 10% weight loss) up to about 470° C.

Melt Processability

Some perfluoro homopolymers and copolymers remains brittle unless processed at a high temperature. Some perfluoro homopolymers and copolymers has poor melt flow characteristic that make them difficult to process even at high temperatures. The perfluoro copolymers of the present disclosure, in some embodiments, have better melt processability at lower temperatures than the corresponding homopolymers.

In some embodiments, the perfluoro copolymer of the present disclosure have better melt processability at lower temperatures than the corresponding homopolymer of the perfluoro dioxole monomer. In some embodiments, the perfluoro copolymer of the present disclosure have better melt processability at lower temperatures than the corresponding homopolymer of the optional perhalo monomer.

In some embodiments, the perfluoro copolymer can be melt processed at a temperature of up to about 420° C. In some embodiments, the perfluoro copolymer can be melt processed at a temperature of up to about 410° C. In some embodiments, the perfluoro copolymer can be melt processed at a temperature of up to about 400° C. In some embodiments, the perfluoro copolymer can be melt processed at a temperature of up to about 380° C.

Gas Permeability/Permeance

One aspect of the perfluoro copolymers of the present disclosure is their improved gas permeability and/or selectivity. Permeability (P) is defined in the following equation with the pressure difference (ΔP), thickness (1), and normalized flux (n):

$$P = \frac{nl}{\Delta P}$$

Permeability has units of Barrer, where 1 Barrer=$10^{-10}$ cm³ (STP) cm/(cm² s cmHg). For asymmetric membranes with an unknown selective layer thickness, the gas permeation property is characterized using the term of permeance (P/l), which is expressed in units of GPU, where 1 GPU=$10^{-6}$ cm³ (STP)/(cm² s cmHg).

In the solution-diffusion model, permeability can be expressed as the product of the concentration averaged diffusion coefficient (D, cm²/s) and the sorption coefficient (S, cm³ (STP) cm$^{-3}$ atm$^{-1}$), which represent the kinetic and thermodynamic components of the transport process, respectively:

$$P = \overline{D} \times S$$

The selectivity, $\alpha_{A/B}$, is defined as the ratio of the permeabilities of two permeating species, A and B:

$$\alpha_{A/B} = \frac{P_A}{P_B} = \frac{D_A}{D_B} \times \frac{S_A}{S_B}$$

where $D_A/D_B$ is the diffusivity selectivity, and $S_A/S_B$ is the solubility selectivity. Modern polymeric membrane materials are designed and engineered by tailoring the sorption and diffusion behavior for selectivity improvement.

Permeance of the perfluoro copolymer can be measured by the following procedure. The perfluoro copolymer is dissolved and painted on a polyethylenimine (PEI) support layer via spray coating. The perfluoro copolymer serves as the selective layer in this composite, which is placed in a stainless-steel cross flow testing cell having a feed port, retentate port, a sweep inlet port, and a permeate port.

The feed port of the cell is connected to a gas manifold consisting of 3 gases: oxygen, nitrogen and hydrogen. The retentate port is connected to a ball valve to dead end the gas flow as well as to purge the gas. One of the two permeate ports is shut and the other is connected to a flow meter. Nitrogen is brought up to pressure by a gas regulator and allowed to purge slowly for 1 minute. The retentate port is closed and a flow measurement can be taken from the permeate which is at atmospheric pressure. This process is repeated for three different feed pressures between 5 to 10 psi so that an average permeance can be calculated. The feed pressure, permeate flowrate, and temperature are recorded for the calculation. The permeance can be calculated by the equation: $Q=F/(A \cdot \Delta P)$ in which Q=gas permeance, F=permeate flow rate, $\Delta P$=transmembrane pressure difference, and A is the effective area of the membrane.

In some embodiments, the perfluoro copolymer has an $O_2$ permeance of at least 4200 GPU. In some embodiments, the perfluoro copolymer has an $O_2$ permeance of at least 4400 GPU. In some embodiments, the perfluoro copolymer has an $O_2$ permeance of at least 4600 GPU. In some embodiments, the perfluoro copolymer has an $O_2$ permeance of at least 4800 GPU. In some embodiments, the perfluoro copolymer has an $O_2$ permeance of at least 5000 GPU.

In some embodiments, the perfluoro copolymer has an $N_2$ permeance of at least 2100 GPU. In some embodiments, the perfluoro copolymer has an $N_2$ permeance of at least 2200 GPU. In some embodiments, the perfluoro copolymer has an $N_2$ permeance of at least 2300 GPU. In some embodiments, the perfluoro copolymer has an $N_2$ permeance of at least 2400 GPU. In some embodiments, the perfluoro copolymer has an $N_2$ permeance of at least 2500 GPU.

In some embodiments, the perfluoro copolymer has an $H_2$ permeance of at least 8000 GPU. In some embodiments, the perfluoro copolymer has an $H_2$ permeance of at least 8500 GPU. In some embodiments, the perfluoro copolymer has an $H_2$ permeance of at least 9000 GPU. In some embodiments, the perfluoro copolymer has an $H_2$ permeance of at least 9500 GPU. In some embodiments, the perfluoro copolymer has an $H_2$ permeance of at least 10000 GPU.

UV Transmittance

One aspect of the perfluoro copolymers of the present disclosure is their better optical property, including high UV transmittance. In some embodiments, the perfluoro copolymer has a 200-500 nm UV transmittance of at least 65%. In some embodiments, the perfluoro copolymer has a 200-500 nm UV transmittance of at least 70%. In some embodiments, the perfluoro copolymer has a 200-500 nm UV transmittance of at least 75%. In some embodiments, the perfluoro copolymer has a 200-500 nm UV transmittance of at least 80%. In some embodiments, the perfluoro copolymer has a 200-500 nm UV transmittance of at least 85%. In some embodiments, the perfluoro copolymer has a 200-500 nm UV transmittance of at least 90%. In some embodiments, the perfluoro copolymer has a 200-500 nm UV transmittance of at least 95%. In some embodiments, the perfluoro copolymer has a 200-500 nm UV transmittance of at least 97%. In some embodiments, the perfluoro copolymer has a 200-500 nm UV transmittance of at least 98%. In some embodiments, the perfluoro copolymer has a 200-500 nm UV transmittance of at least 99%. As show in FIG. 2, UV transmittance of a perfluoro copolymer according to a non-limiting example of the present disclosure has a UV transmittance close to 100%, especially in 300-500 nm.

Method of Making Perfluoro Copolymers

Another aspect of the present disclosure relates to a method of making a perfluoro copolymer disclosed herein, the method comprising: mixing the first monomer, the second monomer, the optional third monomer, and an initiator in a reaction medium to form a polymerization mixture; and initiating polymerization to form the perfluoro copolymer.

In some embodiments, the reaction medium comprises one or more fluorinated solvents. In some embodiments, the one or more fluorinated solvents are selected from Opteon SF79, perfluorooctanoic acid, Vertrel XF, or combinations thereof. The method of claim 89-91, wherein the reaction medium is a solution.

In some embodiments, the reaction medium further comprises water. In some embodiments, the reaction medium is an emulsion.

In some embodiments, the initiator is a free radical initiator. In some embodiments, the initiator is a peroxide initiator. In some embodiments, the initiator is an organic peroxide initiator. In some embodiments, the initiator is selected from perfluoropropionyl peroxide, 4, 4'-bis(t-butylcyclohexyl)peroxy decarbonate, or $(NH4)_2S_2O_8$.

In some embodiments, the polymerization is initiated by heating the polymerization mixture.

In some embodiments, the polymerization mixture is heated at a temperature of from about 50° C. to about 80° C. In some embodiments, the polymerization mixture is heated at a temperature of from about 60° C. to about 75° C.

In some embodiments, the polymerization mixture is heated at a temperature of from about 50° C. to about 80° C. until the perfluoro copolymer is formed. In some embodiments, the polymerization mixture is heated at a temperature of from about 60° C. to about 75° C. until the perfluoro copolymer is formed.

In some embodiments, the polymerization mixture is heated at a temperature of from about 50° C. to about 80° C. until the polymerization is completed. In some embodiments, the polymerization mixture is heated at a temperature of from about 60° C. to about 75° C. until the polymerization is completed.

In some embodiments, the polymerization mixture is heated for a period of from about 4 h to about 24 h. In some embodiments, the polymerization mixture is heated for a period of from about 6 h to about 12 h. In some embodiments, the polymerization mixture is heated in a sealed reaction vessel.

In some embodiments, the method further comprises separating the perfluoro copolymer from the polymerization mixture. In some embodiments, the perfluoro copolymer is separated from the polymerization mixture by removing volatile components of the polymerization mixture through evaporation. In some embodiments, the perfluoro copolymer is separated from the polymerization mixture by adding an anti-solvent to the polymerization mixture to precipitate the perfluoro copolymer. In some embodiments, the anti-solvent is nitric acid.

Article of Manufacture

Another aspect of the present disclosure relates to an article of manufacture, comprising the perfluoro copolymer disclosed herein. In some embodiments, the article of manufacturing is a film formed with the perfluoro copolymer. In some embodiments, the film is a free-standing film.

In some embodiment, the film can be fabricated by providing the perfluoro copolymer typically as a solution in an effective solvent. The concentration of solution can be adjusted by dilution with solvent to obtain optimum fluid viscosity for subsequent steps of fabrication. For many of the perfluoro copolymers of this invention common organic solvents such as acetone, lower alcohols, for example, ethanol and methanol the like, can be used.

As the perfluoro copolymers of the present disclosure have a large proportion of perfluorinated monomer repeating units, fluorosolvents may also be needed in mixture with organic solvents. These fluorosolvents have been identified as being particularly effective for dissolving perfluoropolymers.

In some embodiments, representative fluorosolvents that are suitable for use include FLUORINERT™ FC-75, FC-40, and FC-770 Electronic Liquids, and NOVEC™ HFE-7100, NOVEC™ HFE-7200, and NOVEC™ 7300 Engineered Fluids also from 3M FLUORINERT FC-75 is a solvent of perfluorinated compounds primarily with 8 carbons, believed to include 2-butyltetrahydrofuran. FLUORINERT™ FC770 contains C1-C3 perfluoro N-alkyl morpholines among other perfluorinated compounds. NOVEC™ HFE-7100 includes methyl nonafluoroisobutyl ether and methyl nonafluorobutyl ether. NOVEC™ HFE-7200 includes ethyl nonafluoroisobutyl ether and ethyl nonafluorobutyl ether. NOVEC™ 7300 contains 1,1,1,2,2,3,4,5,5,5-decafluoro-3-methoxy-4-(trifluoromethyl)-pentane. Another suitable fluorosolvent is VERTREL® XF specialty fluid which is 2,3-dihydroperfluoropentane available from DuPont Wilmington, Del.

In some embodiments, a suitable production technique to fabricate a membrane uses the solution from which the solvent is removed to leave a solid membrane structure of the fluorinated copolymer. In some embodiments, the active layer, i.e., the selectively permeable portion, of the membrane is non-porous. The active layer of fluorinated copolymer can be formed from solution to a self-supporting, monolithic film structure by depositing a layer of polymer solution on a releasable substrate, evaporating the solvent and stripping the membrane from the substrate. Usually the minimum thickness to provide structural integrity for a self-supporting, monolithic film of this polymer is so large that pressure gradient across the membrane is too large for most practical selective permeation processes.

In some embodiments, the membrane employed includes a composite structure comprising the active layer and a support layer of a structurally strong, substrate material. The support layer normally is not selectively permeable and typically the substrate material of the support layer is microporous. The substrate is coextensive with and can be in direct contact with the active layer. In the composite membrane, the active layer is made extremely thin to facilitate flow of the migrating mixture components during permeation. The support layer can be laminated on or otherwise affixed to the active layer. Preferably, and especially for hollow fiber membranes the active layer can be solution coated on a surface of the microporous substrate.

In some embodiments, the substrate can be any microporous material that is chemically stable in presence of the feed composition. By "chemically stable" is meant that the substrate is able to maintain its structural integrity without significant deterioration after enduring contact with components of the feed composition. By "microporous" is meant that the structure has pores throughout and that form continuous interstices or passageways extending from one side of the substrate through the thickness to the other side such that the feed can pass through the substrate indiscriminately. Many conventional, readily available and thus generally inexpensive, microporous membrane substrate materials can be used. Representative examples of porous substrate material are polymers selected from the group consisting of polyacrylonitrile (PAN), polyether ether ketone (PEEK), polyvinylidene fluoride (PVDF), polytetrafluoroethylene (PTFE), polypropylene, polysulfone (PSF) and polyether sulfone (PES).

In some embodiments, the composite membranes may include additional layers, such as a layer, sometimes known as a "gutter layer", between the microporous support material and the active, selective layer, or a protective layer on exposed surface of the active layer, i.e., on the side of the active layer opposite the microporous support. A gutter layer typically has multiple purposes. One is to coat the support with a material that seals small defects in the support surface. It also can provide a smooth, substantially completely defect-free surface onto which the selective layer may be coated. Another purpose is to provide a layer of material highly permeable to the compounds being separated so as to channel permeating molecules to the relatively widely spaced pores in the support layer. The protective layer shields the thin active layer from physical damage experienced in normal process operations.

The membrane structure for use with this disclosure can be in a plurality of configurations, such as flat sheet, hollow fiber, tubular, spiral wound and vortex devices (also known as "rotating" devices). Other useful configurations include pleated sheet and tube ribbon form. Hollow fiber composite membranes are much preferred.

The fluorinated copolymer membrane of this invention is used in a method for separation of fluid mixtures by selective permeation. The fluids at atmospheric pressure and temperature conditions are in the state of a gas, a liquid or a combination thereof. Primarily the present method is intended for separation of gas mixtures. A mixture to be separated is placed in contact with one side (i.e., the "feed-retentate side") of the membrane. Conditions on both sides of the membrane, such as temperature, pressure, and partial pressure of the components, are maintained to impose a driving force for the permeation of the components of the feed mixture. The mixture components permeate through the membrane to the opposite, (i.e., "permeate") side of the membrane. The transmembrane migration speeds of individual components differ from each other depending on the permeability property of the individual components and driving force for the individual components, that is, for example, the transmembrane partial pressure difference. In comparison to the composition of the mixture fed to the membrane, a composition enriched in the faster migrating component(s) forms on the permeate side and a composition depleted of the faster migrating component(s) and thus enriched in the slower migrating component(s) forms on the feed-retentate side. The enriched compositions can be recovered for utilitarian purposes.

The membrane of fluorinated copolymer and the method of this invention are useful for separating the components of many chemical mixtures that have substantial industrial importance. Representative gases for which selective permeation through the novel membrane of this invention is considered suitable include the pure components and inorganic compounds oxygen, nitrogen, hydrogen, helium, carbon dioxide, and water vapor. For example, the method can be used to separate such mixtures of these as oxygen/nitrogen, and carbon dioxide/nitrogen. Separation of inorganics from hydrocarbons such as a carbon dioxide/methane blend is contemplated, however separations of hydrocarbons using membranes according to this invention such as separating alkanes or alkenes from alkane/alkene mixtures is not preferred.

This method is deemed especially valuable for producing highly concentrated nitrogen and oxygen products for various commercial uses. The method can be used to separate ordinary air into nitrogen enriched air ("NEA") and/or oxygen enriched air ("OEA"). The combination of oxygen/nitrogen selectivity and oxygen permeance afforded by the present invention is remarkable. The oxygen/nitrogen separation performance is consistently at and sometimes determined to exceed the previously understood theoretical limits.

Non-Limiting Embodiments

The following embodiments are given to enable those skilled in the art to more clearly understand and to practice the present invention. They should not be considered as limiting the scope of the invention, but merely as being illustrative and representative thereof.

1. A perfluoro copolymer of a first monomer, a second monomer, and an optional third monomer,
   wherein the first monomer is a perfluoro dioxole compound,
   wherein the second monomer is a perfluoro compound of Formula I:

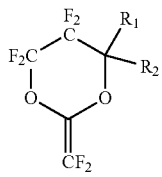

Formula I wherein the $R_1$ and $R_2$ are each independently F or a C1-C4 perfluoro alkyl, provided that $R_1$ and R2 are not the same, and
   wherein the third monomer is selected from: (a) a perhaloolefin wherein each halogen is fluorine or chlorine, provided that at least one half of the halogen atoms must be fluorine, or (b) a perfluoro(alkyl vinyl ether).
2. The perfluoro copolymer of Embodiment 1, wherein the first monomer is selected from perfluoro-2,2-dimethyl-1,3-dioxole, perfluoro-2-fluoro-2-methyl-1,3-dioxole, or perfluoro-1,3-dioxole.
3. The perfluoro copolymer of Embodiment 1, wherein the first monomer is perfluoro-2,2-dimethyl-1,3-dioxole.
4. The perfluoro copolymer of Embodiment 1-3, wherein $R_1$ is F.
5. The perfluoro compound of Embodiment 1-4, wherein $R_2$ is $CF_3$.
6. The perfluoro copolymer of Embodiment 1-5, wherein the first monomer is present at no less than about 30 mole percent, and preferably no less than about 40 mole percent of total moles of all monomers.
7. The perfluoro copolymer of Embodiment 1-5, wherein the first monomer is present at no less than about 45 mole percent of total moles of all monomers.
8. The perfluoro copolymer of Embodiment 1-5, wherein the first monomer is present at no less than about 50 mole percent of total moles of all monomers.
9. The perfluoro copolymer of Embodiment 1-5, wherein the first monomer is present at no less than about 55 mole percent of total moles of all monomers.
10. The perfluoro copolymer of Embodiment 1-5, wherein the first monomer is present at no less than about 60 mole percent of total moles of all monomers.
11. The perfluoro copolymer of Embodiment 1-5, wherein the first monomer is present at no less than about 65 mole percent of total moles of all monomers.
12. The perfluoro copolymer of Embodiment 1-5, wherein the first monomer is present at no less than about 70 mole percent of total moles of all monomers.
13. The perfluoro copolymer of Embodiment 1-5, wherein the first monomer is present at no less than about 75 mole percent of total moles of all monomers.
14. The perfluoro copolymer of Embodiment 1-5, wherein the first monomer is present at no less than about 80 mole percent of total moles of all monomers.
15. The perfluoro copolymer of Embodiment 1-5, wherein the first monomer is present at no less than about 85 mole percent of total moles of all monomers.
16. The perfluoro copolymer of Embodiment 1-5, wherein the first monomer is present at no less than about 90 mole percent of total moles of all monomers.
17. The perfluoro copolymer of Embodiment 1-5, wherein the first monomer is present at no less than about 95 mole percent of total moles of all monomers.
18. The perfluoro copolymer of Embodiment 1-17, wherein the second monomer is present at no more than about 70 mole percent, preferably no more than about 60 mole percent, more preferably no more than about 40 mole percent, and most preferably no more than about 30 mole percent, of total moles of all monomers.
19. The perfluoro copolymer of Embodiment 1-17, wherein the second monomer is present at no more than about 25 mole percent of total moles of all monomers.
20. The perfluoro copolymer of Embodiment 1-17, wherein the second monomer is present at no more than about 20 mole percent of total moles of all monomers.
21. The perfluoro copolymer of Embodiment 1-17, wherein the second monomer is present at no more than about 15 mole percent of total moles of all monomers.
22. The perfluoro copolymer of Embodiment 1-17, wherein the second monomer is present at no more than about 10 mole percent of total moles of all monomers.
23. The perfluoro copolymer of Embodiment 1-17, wherein the second monomer is present at no more than about 5 mole percent of total moles of all monomers.
24. The perfluoro compound of Embodiment 1-23, wherein the third monomer is a perhaloolefin selected from: perhaloolefin selected from tetrafluoroethylene or chlorotrifluoroethylene.
25. The perfluoro compound of Embodiment 1-24, wherein the third monomer is perfluoro(methyl vinyl ether).
26. The perfluoro copolymer of Embodiment 1-25, wherein the third monomer is present at no more than about 40 mole percent based on total moles of all monomers.

27. The perfluoro copolymer of Embodiment 1-25, wherein the third monomer is present at no more than about 35 mole percent based on total moles of all monomers.
28. The perfluoro copolymer of Embodiment 1-25, wherein the third monomer is present at no more than about 30 mole percent based on total moles of all monomers.
29. The perfluoro copolymer of Embodiment 1-25, wherein the third monomer is present at no more than about 25 mole percent based on total moles of all monomers.
30. The perfluoro copolymer of Embodiment 1-25, wherein the third monomer is present at no more than about 20 mole percent based on total moles of all monomers.
31. The perfluoro copolymer of Embodiment 1-25, wherein the third monomer is present at no more than about 15 mole percent based on total moles of all monomers.
32. The perfluoro copolymer of Embodiment 1-25, wherein the third monomer is present at no more than about 10 mole percent based on total moles of all monomers.
33. The perfluoro copolymer of Embodiment 1-25, wherein the third monomer is present at no more than about 5 mole percent based on total moles of all monomers.
34. The perfluoro copolymer of Embodiment 1-25, wherein the third monomer is not present.
35. The perfluoro copolymer of Embodiment 1-34, essentially free of additional monomers that are not one of the first, second, and third monomers.
36. The perfluoro copolymer of Embodiment 1-35, wherein the perfluoro copolymer is amorphous.
37. The perfluoro copolymer of Embodiment 1-36, wherein the perfluoro copolymer has a Tg of at least about 140° C.
38. The perfluoro copolymer of Embodiment 1-36, wherein the perfluoro copolymer has a Tg of at least about 150° C.
39. The perfluoro copolymer of Embodiment 1-36, wherein the perfluoro copolymer has a Tg of at least about 160° C.
40. The perfluoro copolymer of Embodiment 1-36, wherein the perfluoro copolymer has a Tg of at least about 170° C.
41. The perfluoro copolymer of Embodiment 1-36, wherein the perfluoro copolymer has a Tg of at least about 180° C.
42. The perfluoro copolymer of Embodiment 1-36, wherein the perfluoro copolymer has a Tg of at least about 200° C.
43. The perfluoro copolymer of Embodiment 1-36, wherein the perfluoro copolymer has a Tg of at least about 230° C.
44. The perfluoro copolymer of Embodiment 1-36, wherein the perfluoro copolymer has a Tg of at least about 240° C.
45. The perfluoro copolymer of Embodiment 1-44, wherein the perfluoro copolymer has a Tg of no more than about 250° C.
46. The perfluoro copolymer of Embodiment 1-44, wherein the perfluoro copolymer has a Tg of no more than about 260° C.
47. The perfluoro copolymer of Embodiment 1-44, wherein the perfluoro copolymer has a Tg of no more than about 270° C.
48. The perfluoro copolymer of Embodiment 1-44, wherein the perfluoro copolymer has a Tg of no more than about 280° C.
49. The perfluoro copolymer of Embodiment 1-44, wherein the perfluoro copolymer has a Tg of no more than about 290° C.
50. The perfluoro copolymer of Embodiment 1-44, wherein the perfluoro copolymer has a Tg of no more than about 300° C.
51. The perfluoro copolymer of Embodiment 1-44, wherein the perfluoro copolymer has a Tg of no more than about 310° C.
52. The perfluoro copolymer of Embodiment 1-44, wherein the perfluoro copolymer has a Tg of no more than about 320° C.
53. The perfluoro copolymer of Embodiment 1-44, wherein the perfluoro copolymer has a Tg of no more than about 330° C.
54. The perfluoro copolymer of Embodiment 1-53, wherein the perfluoro copolymer has an FC-75 solubility of up to about 10 wt %.
55. The perfluoro copolymer of Embodiment 1-53, wherein the perfluoro copolymer has an FC-75 solubility of up to about 8 wt %.
56. The perfluoro copolymer of Embodiment 1-53, wherein the perfluoro copolymer has an FC-75 solubility of up to about 6 wt %.
57. The perfluoro copolymer of Embodiment 1-53, wherein the perfluoro copolymer has an FC-75 solubility of up to about 5 wt %.
58. The perfluoro copolymer of Embodiment 1-53, wherein the perfluoro copolymer has an FC-75 solubility of up to about 4 wt %.
59. The perfluoro copolymer of Embodiment 1-53, wherein the perfluoro copolymer has an FC-75 solubility of up to about 3 wt %.
60. The perfluoro copolymer of Embodiment 1-53, wherein the perfluoro copolymer has an FC-75 solubility of up to about 2 wt %.
61. The perfluoro copolymer of Embodiment 1-60, wherein the perfluoro copolymer has an FC-40 solubility of up to about 2 wt %.
62. The perfluoro copolymer of Embodiment 1-60, wherein the perfluoro copolymer has an FC-40 solubility of up to about 1 wt %.
63. The perfluoro copolymer of Embodiment 1-62, wherein the perfluoro copolymer is stable up to about 420° C.
64. The perfluoro copolymer of Embodiment 1-62, wherein the perfluoro copolymer is stable up to about 430° C.
65. The perfluoro copolymer of Embodiment 1-62, wherein the perfluoro copolymer is stable up to about 440° C.
66. The perfluoro copolymer of Embodiment 1-62, wherein the perfluoro copolymer is stable up to about 450° C.
67. The perfluoro copolymer of Embodiment 1-62, wherein the perfluoro copolymer is stable up to about 460° C.
68. The perfluoro copolymer of Embodiment 1-62, wherein the perfluoro copolymer is stable up to about 470° C.

69. The perfluoro copolymer of Embodiment 1-68, wherein the perfluoro copolymer can be processed at a temperature of up to about 420° C.
70. The perfluoro copolymer of Embodiment 1-68, wherein the perfluoro copolymer can be processed at a temperature of up to about 410° C.
71. The perfluoro copolymer of Embodiment 1-68, wherein the perfluoro copolymer can be processed at a temperature of up to about 400° C.
72. The perfluoro copolymer of Embodiment 1-68, wherein the perfluoro copolymer can be processed at a temperature of up to about 380° C.
73. The perfluoro copolymer of Embodiment 1-72, wherein the perfluoro copolymer has an $O_2$ permeance of at least 4200 GPU.
74. The perfluoro copolymer of Embodiment 1-72, wherein the perfluoro copolymer has an $O_2$ permeance of at least 4400 GPU.
75. The perfluoro copolymer of Embodiment 1-72, wherein the perfluoro copolymer has an $O_2$ permeance of at least 4600 GPU.
76. The perfluoro copolymer of Embodiment 1-72, wherein the perfluoro copolymer has an $O_2$ permeance of at least 4800 GPU.
77. The perfluoro copolymer of Embodiment 1-72, wherein the perfluoro copolymer has an $O_2$ permeance of at least 5000 GPU.
78. The perfluoro copolymer of Embodiment 1-77, wherein the perfluoro copolymer has an $N_2$ permeance of at least 2100 GPU.
79. The perfluoro copolymer of Embodiment 1-77, wherein the perfluoro copolymer has an $N_2$ permeance of at least 2200 GPU.
80. The perfluoro copolymer of Embodiment 1-77, wherein the perfluoro copolymer has an $N_2$ permeance of at least 2300 GPU.
81. The perfluoro copolymer of Embodiment 1-77, wherein the perfluoro copolymer has an $N_2$ permeance of at least 2400 GPU.
82. The perfluoro copolymer of Embodiment 1-77, wherein the perfluoro copolymer has an $N_2$ permeance of at least 2500 GPU.
83. The perfluoro copolymer of Embodiment 1-82, wherein the perfluoro copolymer has an $H_2$ permeance of at least 8000 GPU.
84. The perfluoro copolymer of Embodiment 1-82, wherein the perfluoro copolymer has an $H_2$ permeance of at least 8500 GPU.
85. The perfluoro copolymer of Embodiment 1-82, wherein the perfluoro copolymer has an $H_2$ permeance of at least 9000 GPU.
86. The perfluoro copolymer of Embodiment 1-82, wherein the perfluoro copolymer has an $H_2$ permeance of at least 9500 GPU.
87. The perfluoro copolymer of Embodiment 1-82, wherein the perfluoro copolymer has an $H_2$ permeance of at least 10000 GPU.
88. The perfluoro copolymer of Embodiment 1-82, wherein the first monomer is perfluoro-2,2-dimethyl-1,3-dioxole, wherein the second monomer is perfluoro-2-methylene-4-methyl-1,3-dioxane, and wherein the perfluoro copolymer is essentially free of additional monomers that are not one of the first and second monomers.
89. A method of making a perfluoro copolymer of Embodiment 1-88, the method comprising:
  mixing the first monomer, the second monomer, the optional third monomer, and an initiator in a reaction medium to form a polymerization mixture;
  initiating polymerization to form the perfluoro copolymer.
90. The method of Embodiment 89, wherein the reaction medium comprises one or more fluorinated solvents.
91. The method of Embodiment 90, wherein the one or more fluorinated solvents are selected from Opteon SF79, perfluorooctanoic acid, Vertrel XF, or combinations thereof
92. The method of Embodiment 89-91, wherein the reaction medium is a solution.
93. The method of Embodiment 90-91, wherein the reaction medium further comprises water.
94. The method of Embodiment 94, wherein the reaction medium is an emulsion.
95. The method of Embodiment 89-94, wherein the initiator is a free radical initiator.
96. The method of Embodiment 89-94, wherein the initiator is a peroxide initiator.
97. The method of Embodiment 89-94, wherein the initiator is an organic peroxide initiator.
98. The method of Embodiment 89-94, wherein the initiator is selected from perfluoropropionyl peroxide, 4, 4'-bis(t-butylcyclohexyl)peroxydicarbonate, or $(NH4)_2S_2O_8$.
99. The method of Embodiment 89-98, wherein the polymerization is initiated by heating the polymerization mixture.
100. The method of Embodiment 99, wherein the polymerization mixture is heated at a temperature of from about 50° C. to about 80° C.
101. The method of Embodiment 99, wherein the polymerization mixture is heated at a temperature of from about 60° C. to about 75° C.
102. The method of Embodiment 99-101, wherein the polymerization mixture is heated at a temperature of from about 50° C. to about 80° C. until the perfluoro copolymer is formed.
103. The method of Embodiment 99-101, wherein the polymerization mixture is heated at a temperature of from about 60° C. to about 75° C. until the perfluoro copolymer is formed.
104. The method of Embodiment 99-103, wherein the polymerization mixture is heated at a temperature of from about 50° C. to about 80° C. until the polymerization is completed.
105. The method of Embodiment 99-103, wherein the polymerization mixture is heated at a temperature of from about 60° C. to about 75° C. until the polymerization is completed.
106. The method of Embodiment 99-105, wherein the polymerization mixture is heated for a period of from about 4 h to about 24 h.
107. The method of Embodiment 99-105, wherein the polymerization mixture is heated for a period of from about 6 h to about 12 h.
108. The method of Embodiment 89-107, wherein the polymerization mixture is contacted with fluorine gas after completion of polymerization.
109. The method of Embodiment 89-108, further comprising separating the perfluoro copolymer from the polymerization mixture.
110. The method of Embodiment 109, wherein the perfluoro copolymer is separated from the polymerization mixture by removing volatile components of the polymerization mixture through evaporation.

111. The method of Embodiment 109, wherein the perfluoro copolymer is separated from the polymerization mixture by adding an anti-solvent to the polymerization mixture to precipitate the perfluoro copolymer.

112. The method of Embodiment 111, wherein the anti-solvent is nitric acid.

113. An article of manufacturing, comprising the perfluoro copolymer of Embodiment 1-112.

114. The article of Embodiment 113, comprising a film formed with the perfluoro copolymer.

115. The article of Embodiment 114, wherein the film is a free-standing film.

116. A perfluoro compound of Formula I:

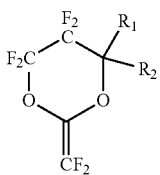

Formula I wherein the $R_1$ and $R_2$ are each independently F or a C1-C4 perfluoro alkyl, provided that R1 and R2 are not the same.

117. The perfluoro compound of Embodiment 116, wherein $R_1$ is F.

118. The perfluoro compound of Embodiment 116-117, wherein $R_2$ is $CF_3$.

119. The perfluoro compound of Embodiment 116-118, in neat liquid form.

120. A perfluoro compound of Formula II:

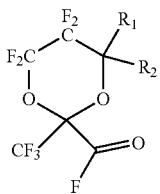

Formula II wherein the $R_1$ and $R_2$ are each independently F or a C1-C4 perfluoro alkyl, provided that $R_1$ and R2 are not the same.

121. The perfluoro compound of Embodiment 120, wherein $R_1$ is F.

122. The perfluoro compound of Embodiment 120-121, wherein $R_2$ is $CF_3$.

123. The perfluoro compound of Embodiment 120-122, in neat liquid form.

NON-LIMITING EXAMPLES

The following examples are provided to illustrate selected embodiments. They should not be considered as limiting the scope of the invention, but merely as being illustrative and representative thereof. Thus, the examples provided below, while illustrated with a particular medical device or active agent, are applicable to the range of medical devices and active agents described herein.

Example 1

Perfluoro-2-methylene-4-methyl-1,3-dioxane (PMX) were synthesized as follows:

Step I: Hydrocarbon Precursor

A reaction mixture: 1.0 mol of 1,3-butanediol, 1.0 mol of methyl pyruvate, 8 g of a cation exchange resin, and 1 L of toluene were refluxed for 4.5 hours, obtaining 2,4-dimethyl-2-carboxymethyl-1,3-dioxane. The yield was 70% and the boiling point of the product was 45° C./1.0 mmHg.

Step II: Fluoride Intermediate

A 10 L stirring-reactor nickel vessel was loaded with 4 liters of Vertrel® XF (trade name). The nitrogen flow was set at 1200 cc/min and the fluorine flow was set at 280 cc/min, thereby making the interior of the stirring-reactor vessel under a nitrogen/fluorine atmosphere. After 5 minutes, 200 g of precursor was dissolved to 500 ml of Vertrel® XF solution, and then this solution was added into the reactor at a rate of 0.5 ml/min. The reactor vessel was cooled to −5° C. After all the precursor was added over 16 hours, the fluorine flow was stopped. The system was purged with nitrogen gas for 30 min. Perfluoro-2,4-dimethyl-2-fluoroformyl-1,3-dioxane was distilled at 68.5° C. in 78% yield.

Step III: perfluoro-2-methylene-4-methyl-1,3-dioxane (PMX)

Perfluoro-2,4-dimethyl-2-fluoroformyl-1,3-dioxane was passed through a loosely packed bed of 8-14 mesh dried sodium carbonate in an 50×3 cm diameter vertical Pyrex tube maintained at a temperature of 300° C. in a current of nitrogen. The perfluoro-2,4-dimethyl-2-fluoroformyl-1,3-dioxane was fed at a rate of 0.03 mole per hour and the nitrogen was fed at a rate of 100 ml per minute. The contact time was thus about 30 seconds. The product gas collected in a cold trap and consisted of PMX, boiling point 58° C. The yield was 93%.

Example 2

A stainless-steel shaker tube was charged with 150 mL FC-72 (3M™ FLUORINERT™ Electronic Liquid), 40 g PDD, 8 g PMX and 5 mL 3% perfluoropropionyl peroxide (PPP) in FC-72. The tube was heated at 60° C. for 6 hours at 60° C. After the tube was purged with nitrogen for 30 minutes, the solvent and excess volatile components were removed by evaporation and the resulting polymer dried at 100° C. under vacuum for 24 hours to yield 38 g (79% conversion) polymer. The copolymer composition was shown by 19F-NMR to be 91 mole % PDD and 9 mole % PMX. The higher PDD content in copolymer product compared to monomer feed ratio can be a result of PDD's better chain propagation activity. The polymer was pressed into a tough and clear film at 370° C. Its Tg was 245° C. Refractive index was 1.311, measured on the pressed film.

Acid fluoride group concentration in PMX/PDD copolymers was measured by Fourier transform infrared spectroscopy (FTIR), the acid fluoride (—COF) band at 1883-1887 $cm^{-1}$ was be identified. In some embodiments, the polymer powder was treated with fluorine gas to further eliminate the acid fluoride end groups and other impurities. Deep fluorination was carried out as follows: 38 g copolymer was placed in a nikel chamber which was evacuated, purged with nitrogen, and then heated to 150° C. A 30/70 v/v fluorine/nitrogen gas mixture was slowly passed over the copolymer for 10 hours while maintaining the 150° C. temperature. The gas flow amounted to 0.05 part of fluorine per part of copolymer. The fluorination chamber was then cooled and purged with nitrogen, and the copolymer was dried in vacuum oven at 100° C. for 24 hours and no obvious weight change was observed. The acid fluoride (—COF) band at 1883-1887 cm$^{-1}$ disappeared based on FTIR analysis.

Figure 2:
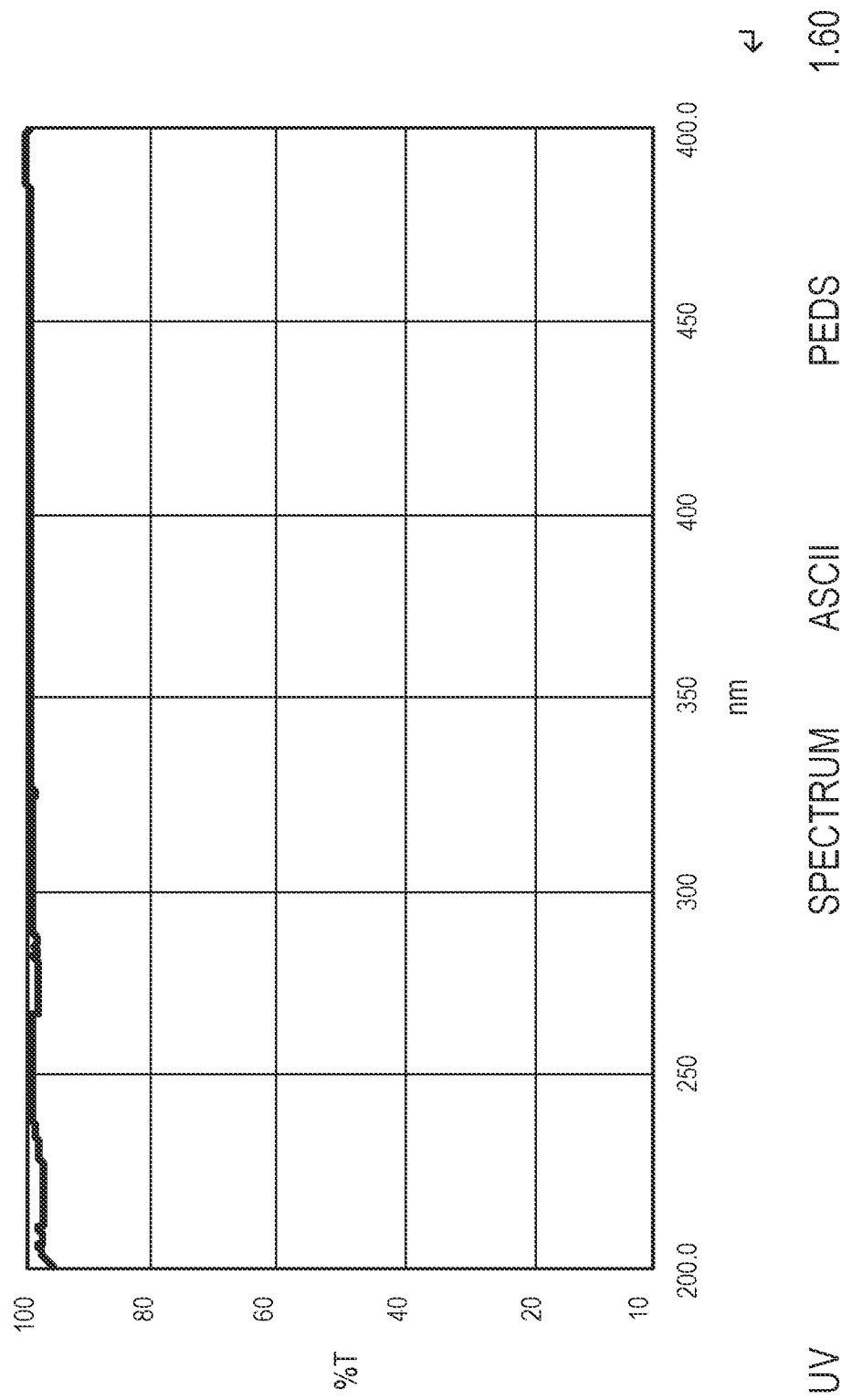
FIG. 2 illustrates UV transmittance of a perfluoro copolymer according to a non-limiting embodiment.
Figure 3:
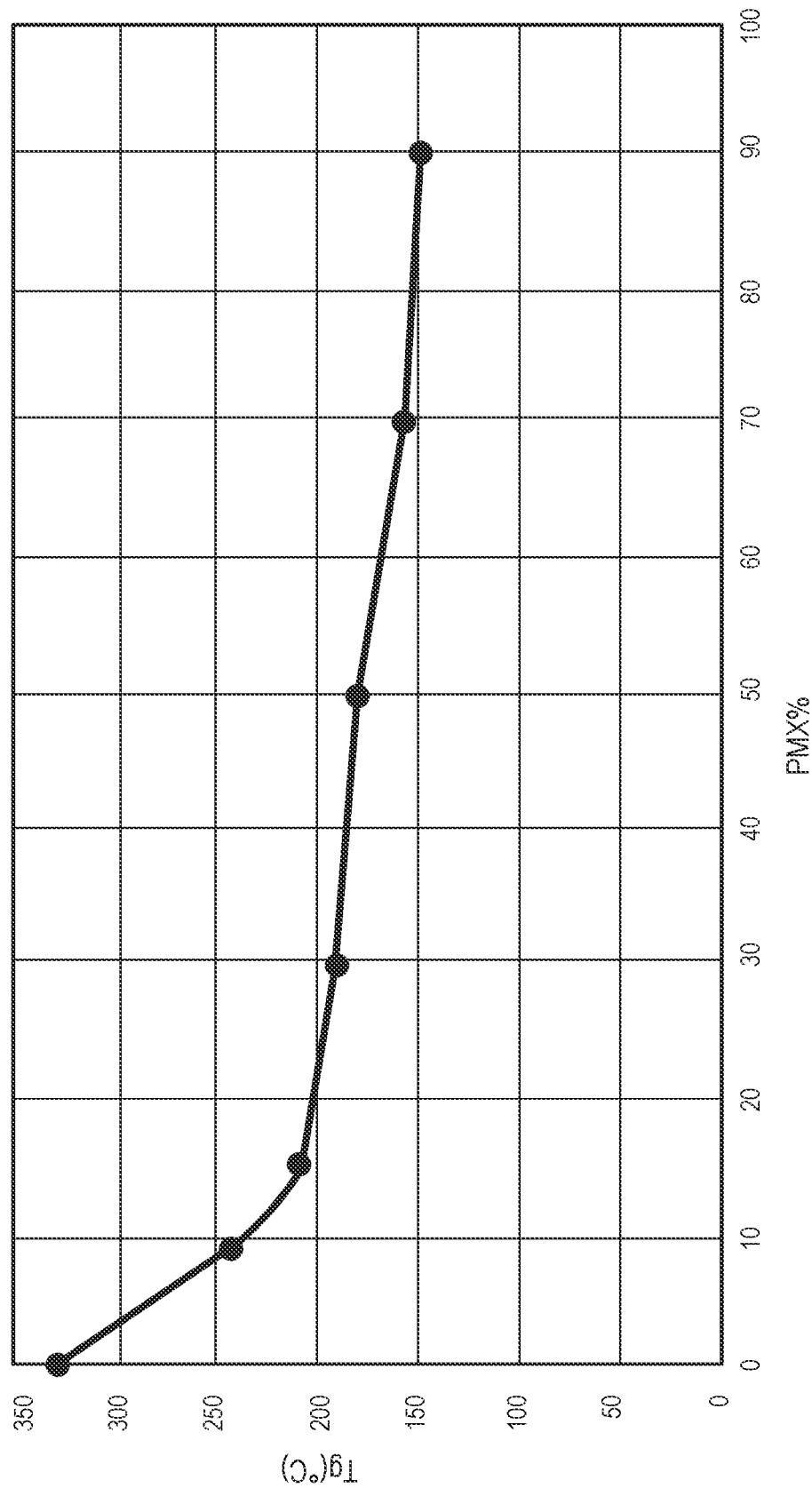
FIG. 3 illustrates correlating of Tg (° C.) and relative amount of PMX in a PDD-PMX copolymer according to a non-limiting embodiment.

The copolymer was soluble to an extent of up to 1% by weight in FLUORINERT® FC-40 at ambient temperature. A 1% solution of the copolymer in FC-40 was painted onto a glass plate and air-dried. The plate was placed in boiling water where the film delaminated. The film was dried at 120° C. in a vacuum oven. Film thickness was about 0.004 mm. As shown in FIG. 2, the film's UV transmittance was tested and nearly no UV absorption was observed. Based on the TGA result shown in FIG. 1, the copolymer's decomposition temperature in the air is higher than 440° C.

Example 3

To test the material's gas permeability, a 0.35% solution of this copolymer was painted on a polyethylenimine (PEI) support layer via spray coating. The copolymer served as the selective layer in this nano-scale composite membrane. For comparison, a series of composite membranes were made using TEFLON® AF2400, HYFLON® AD60 and CYTOP®. The gas permeability results are summarized in Table 1 below:

TABLE 1

| Selective layer | Permeance (GPU) | | | Selectivity | |
| --- | --- | --- | --- | --- | --- |
| polymer | $O_2$ | $N_2$ | $H_2$ | $O_2/N_2$ | $H_2/O_2$ |
| PDD-PMX copolymer | 5100 | 2550 | 10300 | 2 | 2.02 |
| TEFLON® AF2400 | 4150 | 2000 | 7760 | 2.075 | 1.87 |
| HYFLON® AD60 | 360 | 150 | 1420 | 2.4 | 3.94 |
| CYTOP® | 37 | 14 | 226 | 2.64 | 6.1 |

As shown in Table 1, this PDD-PMX copolymer show higher gas permeability than all other commercial perfluoropolymers. Combining its good fabricability, high transparency and extremely low surface energy, the material is a highly competitive candidate for oxygen permeable film and oxygen enrichment monitor sensor etc.

Example 4

In a 200 mL stainless steel tube was charged PDD monomer 5 g, PMX monomer 20 g, Opteon® SF79 100 g, and 4,4'-bis(t-butylcyclohexyl) peroxy dicarbonate (0.05 g). The tube was cooled, evacuated and heated at 70° C. for 8 hours. The solvent was removed and the residual polymer was dried in a vacuum oven at 100° C. for 24 hours to yield 13.7 g (55% conversion) of white powder. This copolymer had a Tg at 160° C. and the composition was determined to be PMX/PDD=68/32 (mol %) by 19F-NMR.

Example 5

To a 200 ml stainless steel tube was charged PMX 10 g, PDD 10 g, perfluorooctanoic acid 0.5 g, (NH4)2S2O8 0.6 g, and 60 ml distilled water. The tube was purged with N2 and sealed. The tube was then heated at 75° C. with vigorous shaking for 8 hours. The reaction mixture was treated with 30 ml nitric acid to precipitate the copolymer. The product was rinsed in a blender with water (3×200 mL) and acetone (3×200 mL). The copolymer was then dried in a vacuum oven at 150° C. for 24 hours to yield white powder 9.6 g (48% conversion). This copolymer had a Tg at 173° C. and a solubility of 3-4 wt % in FC-75.

Example 6

In a 200 mL stainless steel tube was charged PDD monomer 5 g, PMX monomer 5 g, OPTEON®SF79 60 g, and 4,4'-bis(t-butylcyclohexyl) peroxy dicarbonate (0.03 g). The tube was cooled, evacuated and tetrafluoroethylene (TFE) 1 g was transferred into the tube. The tube was then sealed and heated at 70° C. for 8 hours. The solvent was removed and the residual polymer was dried in a vacuum oven at 100° C. for 24 hours to yield 4.96 g (45% conversion) of white powder. This copolymer had a Tg at 142° C. and the composition was determined to be PDD/PMX/TFE=40.6/34.2/25.2 (mol %) by 19F-NMR. Solutions of 4 to 5 wt % of the copolymer in FC-75 were prepared.

Example 7

To a 200 ml stainless steel tube was charged PMX 8 g, PDD 8 g, perfluorooctanoic acid 0.5 g, (NH4)2S2O8 0.6 g, and 60 ml distilled water. The tube was purged with $N_2$ and tetrafluoroethylene (TFE) 1.6 g was transferred into the tube. The tube was then sealed and heated at 75° C. with vigorous shaking for 8 hours. The reaction mixture was treated with 30 ml nitric acid to precipitate the copolymer. The product was rinsed in a blender with water (3×200 mL) and acetone (3×200 mL). The copolymer was then dried in a vacuum oven at 150° C. for 24 hours to yield white powder 9.3 g (53% conversion). This copolymer had a Tg at 142° C. and the composition was determined to be PDD/PMX/TFE=40.2/32.7/27.1 (mol %) by 19F-NMR. Solutions of 4 to 5 wt % of the copolymer in FC-75 were prepared.

Example 8

In a 200 mL stainless steel tube was charged PDD monomer 16 g, PMX monomer 4 g, Vertrel® XF 80 g, and 5 mL 3% perfluoropropionyl peroxide (PPP) in FC-72. The tube was cooled, evacuated and chlorotrifluoroethylene (CTFE) 4 g was transferred into the tube. The tube was then sealed and heated at 60° C. for 8 hours. After evaporation of volatile materials, the white residue was dried under vacuum at 150° C. for 24 hours to give 12.5 g (52% conversion) of copolymer. The 19F-NMR spectrum was consistent with a terpolymer containing 60.2 mol % of PDD, 2.2 mol % of PMX, and 37.6% mol % of CTFE. The copolymer had a Tg of 159° C. and a solubility of 5-6 wt % in FC-75.

Example 9

To a 200 ml stainless steel tube was charged PMX 5 g, PDD 20 g, perfluoro(methyl vinyl ether) (PMVE) 10 g, perfluorooctanoic acid 1 g, (NH4)2S2O8 0.8 g, and 100 ml distilled water. The tube was purged with N2 and sealed. The polymerization was carried out at 75° C. with vigorous shaking for 12 hours. The reaction mixture was treated with 35 ml nitric acid to precipitate the copolymer. The product was rinsed in a blender with water (3×200 mL) and acetone (3×200 mL). The copolymer was then dried in a vacuum oven at 150° C. for 24 hours to yield white powder 14.3 g (41% conversion). This copolymer had a Tg at 168° C. and the composition was determined to be PDD/PMX/PMVE=79.4/7.8/12.8 (mol %) by 19F-NMR.

While preferred embodiments of the present invention have been shown and described herein, it will be obvious to

What is claimed:

1. A perfluoro compound of Formula 1:

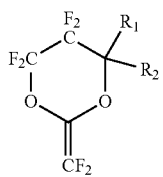

Formula I wherein the $R_1$ and $R_2$ are each independently F or a C1-C4 perfluoro alkyl, provided that R1 and R2 are not the same.

2. The perfluoro compound of claim 1, wherein $R_1$ is F.

3. The perfluoro compound of claim 1, wherein $R_2$ is $CF_3$.

4. A perfluoro copolymer of monomers comprising a first monomer and a second monomer, wherein the first monomer is a perfluoro dioxole compound, and wherein the second monomer is the perfluoro compound of claim 1.

5. The perfluoro copolymer of claim 4, wherein the perfluoro dioxole compound is selected from perfluoro-2,2-dimethyl-1,3-dioxole, perfluoro-2-fluoro-2-methyl-1,3-dioxole, or perfluoro-1,3-dioxole.

6. The perfluoro copolymer of claim 4, wherein the perfluoro dioxole compound is perfluoro-2,2-dimethyl-1,3-dioxole.

7. The perfluoro copolymer of claim 4, wherein the first monomer is present at no less than about 30 mole percent of total moles of all monomers of the perfluoro copolymer.

8. The perfluoro copolymer of claim 4, wherein the second monomer is present at no more than about 70 mole percent of total moles of all monomers of the perfluoro copolymer.

9. A perfluoro copolymer of monomers comprising a first monomer and a second monomer, wherein the first monomer is the perfluoro compound of claim 1, and wherein the second monomer is selected from: (a) a perhaloolefin wherein each halogen is fluorine or chlorine, provided that at least one half of the halogen atoms must be fluorine, or (b) a perfluoro(alkyl vinyl ether).

10. The perfluoro copolymer of claim 9, wherein the second monomer is a perhaloolefin selected from tetrafluoroethylene or chlorotrifluoroethylene.

11. The perfluoro copolymer of claim 9, wherein the second monomer is perfluoro(methyl vinyl ether).

12. The perfluoro copolymer of claim 9, wherein the first monomer is present at no more than about 70 mole percent of total moles of all monomers of the perfluoro copolymer.

13. The perfluoro copolymer of claim 9, wherein the second monomer is present at no more than about 40 mole percent based on total moles of all monomers of the perfluoro copolymer.

14. A perfluoro copolymer of monomers comprising a first monomer, a second monomer, and a third monomer, wherein the first monomer is a perfluoro dioxole compound, and wherein the second monomer is the perfluoro compound of claim 1.

15. The perfluoro copolymer of claim 14, wherein the perfluoro dioxole compound is selected from perfluoro-2,2-dimethyl-1,3-dioxole, perfluoro-2-fluoro-2-methyl-1,3-dioxole, or perfluoro-1,3-dioxole.

16. The perfluoro copolymer of claim 14, wherein the third monomer is selected from: (a) a perhaloolefin wherein each halogen is fluorine or chlorine, provided that at least one half of the halogen atoms must be fluorine, or (b) a perfluoro(alkyl vinyl ether).

17. The perfluoro compound of claim 14, wherein the third monomer is perfluoro(methyl vinyl ether) or a perhaloolefin selected from tetrafluoroethylene or chi orotrifluoroethylene.

18. The perfluoro copolymer of claim 14, wherein the first monomer is present at no less than about 30 mole percent of total moles of all monomers of the perfluoro copolymer.

19. The perfluoro copolymer of claim 14, wherein the second monomer is present at no more than about 70 mole percent of total moles of all monomers of the perfluoro copolymer.

20. The perfluoro copolymer of claim 14, wherein the third monomer is present at no more than about 40 mole percent based on total moles of all monomers of the perfluoro copolymer.

* * * * *